United States Patent [19]

Torre

[11] Patent Number: 5,007,920

[45] Date of Patent: Apr. 16, 1991

[54] TENDON SECTIONING SUPPORT CLAMP

[76] Inventor: Randall J. Torre, 842 S. Clover, San Jose, Calif. 95128

[21] Appl. No.: 328,492

[22] Filed: Mar. 24, 1989

[51] Int. Cl.⁵ .............................................. A61B 17/28
[52] U.S. Cl. ..................................... 606/207; 606/151
[58] Field of Search ........... 128/321, 346, 354, 303 R; 81/312, 418, 420, 424.5, 426; 606/120, 151, 157, 205, 207; 433/159

[56] References Cited

U.S. PATENT DOCUMENTS

| | | | |
|---|---|---|---|
| 1,484,222 | 2/1924 | Kightlinger | 81/420 |
| 1,586,645 | 6/1926 | Bierman | 128/321 |
| 3,304,818 | 2/1967 | Heaton | 81/420 |
| 4,286,598 | 9/1981 | Kopitanov et al. | 606/207 |
| 4,655,223 | 4/1957 | Kim | 128/321 |
| 4,724,838 | 2/1988 | Hasson | 128/321 |

Primary Examiner—C. Fred Rosenbaum
Assistant Examiner—William W. Lewis
Attorney, Agent, or Firm—Schroeder, Davis & Orliss Inc.

[57] ABSTRACT

A tendon or other smooth muscle support clamp which separates to pass around the tissue to be operated upon and supports said tissue by surrounding it on three sides by the walls and bottom of a channel in the upper surface of a support block is provided. The clamp provides a firm support base without risk of trauma to the tissue due to clamping pressure. The clamp resembles a conventional pliers-like surgical forcep but employs either fixed or detachable support blocks with lengthwise channels of various dimensions suitable for a variety of applications.

7 Claims, 4 Drawing Sheets

TENDON SECTIONING SUPPORT CLAMP

BACKGROUND OF THE INVENTION

The present invention relates generally to surgical instruments and, more particularly, to a clamp having a channelled support plate which is utilized to support a tendon or other smooth muscle during a transectioning procedure.

In performing the surgical procedure widely known as a tendon transection, an incision in a tendon or other smooth muscle is made with a scalpel or other suitable surgical instrument to lengthen the tendon or affect some other desired repair. During this surgical procedure it is necessary to have the tendon exposed and accessible and sufficiently supported to perform the desired procedure.

It is well-known in the prior art to provide special purpose clamping apparatus for grasping and supporting skin, bones and other parts of the body for use during surgical procedures. Typically, prior art devices utilize plier- or forceps-like apparatus having opposed fingers or plate-like jaws to surround and grasp or grip a desired body part. The clamping of grasping action is manually applied by action of pivotable handles and is maintained by a ratchet mechanism coupling the handles together or a thumbscrew arrangement. For example, Russian Patent No. 244,559 describes forceps having removeable bosses mounted at the distal ends of the scissor-like arm with bayonet fittings. The bosses have channelled and opposing faces which allow grasping and holding a blood vessel for suturing without interrupting or restricting the blood flow therein.

SUMMARY OF THE INVENTION

In accordance with the principles of the present invention, a tendon support clamp comprises an apparatus having a configuration similar to a pair of pliers with a pair of plates attached at the distal ends and oriented at substantially right angles to the plier arms. A lateral or outside plate is essentially a rectangular shaped rod attached to one of the plier arms and a support plate is attached to the other plier arm at an adjacent end. The support plate is a generally flat, rectangular plate having a groove or channel formed lengthwise in its upper or top surface. The lateral and support plates each have an inwardly facing face in opposing relationship with the other plate and are disposed in spaced apart relationship when the clamp is in an open configuration. When the clamp is in a closed configuration, the opposing faces of the plates are in contact and clamped together. Each plier arm comprises a handle portion at its proximal end to facilitate a user grasping and operating the clamp. The handle portions are coupled together by a ratchet mechanism disposed therebetween which, when engaged prevents the clamp from opening. To use the tendon support clamp, the clamp is opened and applied to an exposed tendon allowing the tendon to pass through the open space between the plates. The clamp is then positioned such that the tendon lays in the channel in the upper surface of the support plate. The clamp is then closed and the rachet mechanism engaged thus maintaining the clamp in a closed configuration and allowing the user free use of both of his or her hands. In this manner, the tendon is supported while an incision or other repair is affected. The tendon support is fabricated from stainless steel and several different support plate sizes will be available.

DETAILED DESCRIPTION OF THE PREFERRED EMBODIMENT

Figure 1:
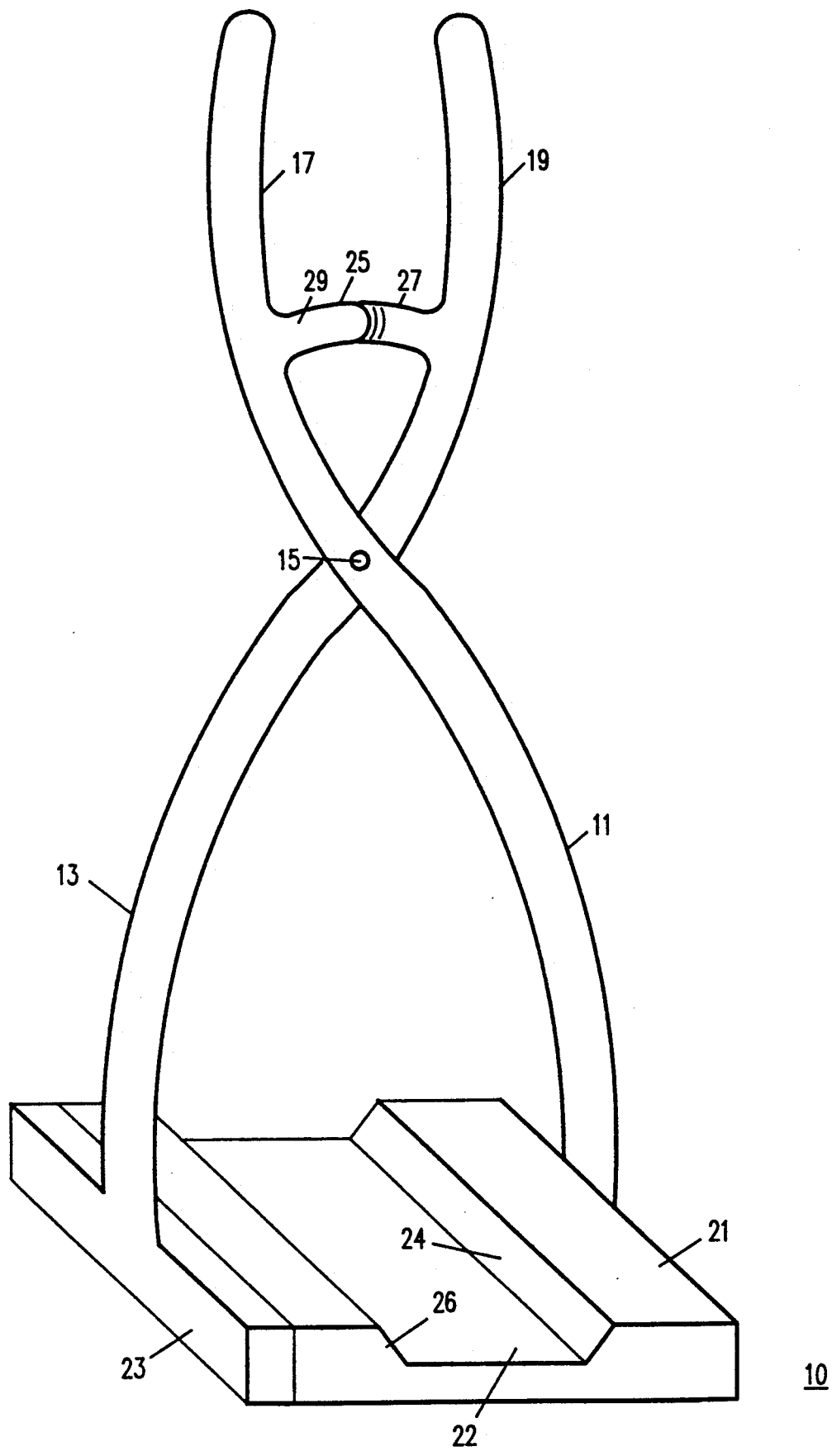
FIG. 1 is a perspective view of a tendon support clamp constructed in accordance with the principles of the present invention.
Figure 2:
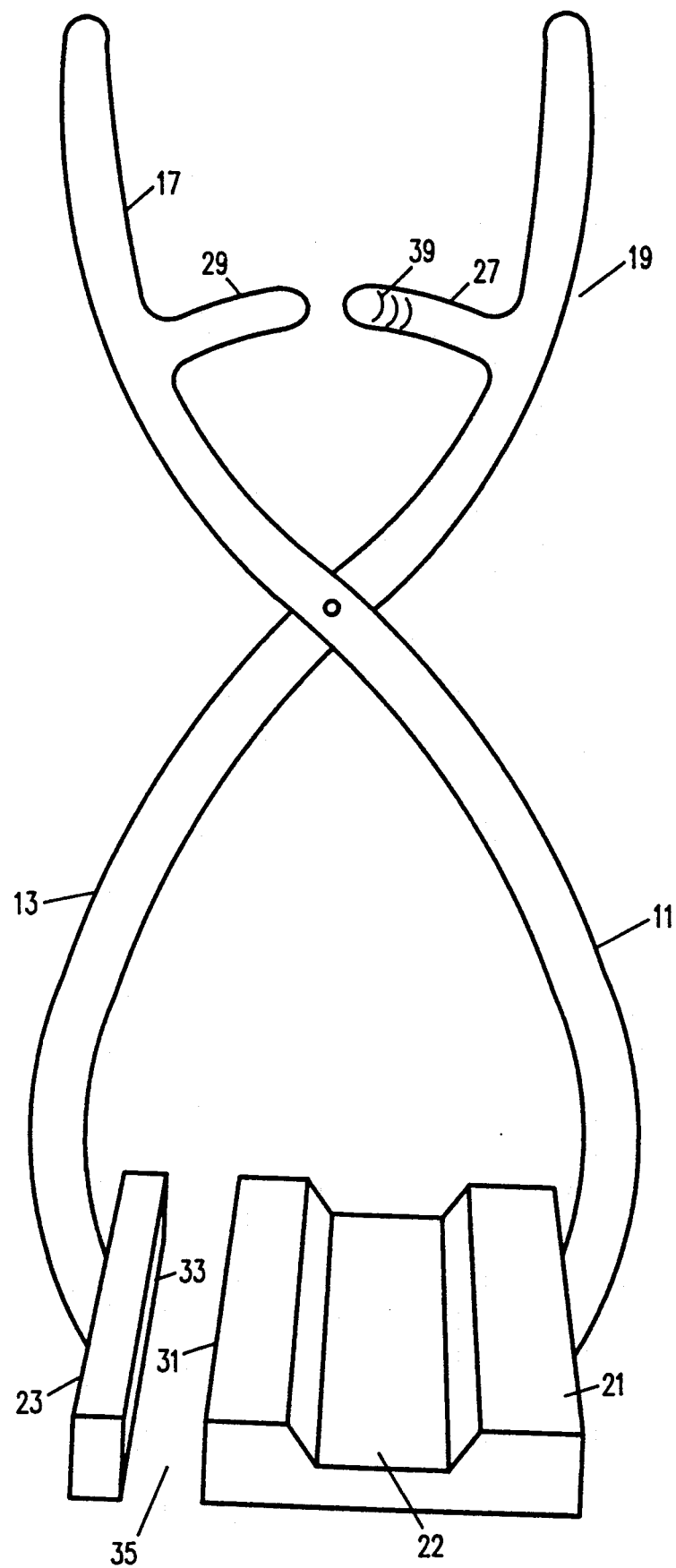
FIG. 2 is a perspective view of the tendon support clamp shown in FIG. 1 illustrating the ratchet mechanism.

Referring now to FIGS. 1 and 2, a tendon support clamp according to the principles of the present invention is shown. The tendon support clamp 10 comprises a pair of longitudinal plier arms 11 and 13 which intersect approximately midway between their ends at a pivot bearing 15. The plier arms 11, 13 each have, at the proximal ends thereof, handle portions 17 and 19, respectively, and a pair of plates 21 and 23, respectively, at the other, distal ends thereof. Intermediate the handle portions 17 and 19, a ratchet mechanism 25 is disposed comprising a ratchet arm 27 integral with one plier arm 13 and a ratchet catch 29 integral with the other plier arm 11.

Each of the plates 21, 23 may be integral with or removeably attached to its associated plier arm 11, 13, respectively, and is oriented at approximately a right angle with respect to its associated plier arm. The plates 21, 23 are mounted so as to be longitudinally parallel and substantially coplanar.

Figure 3:
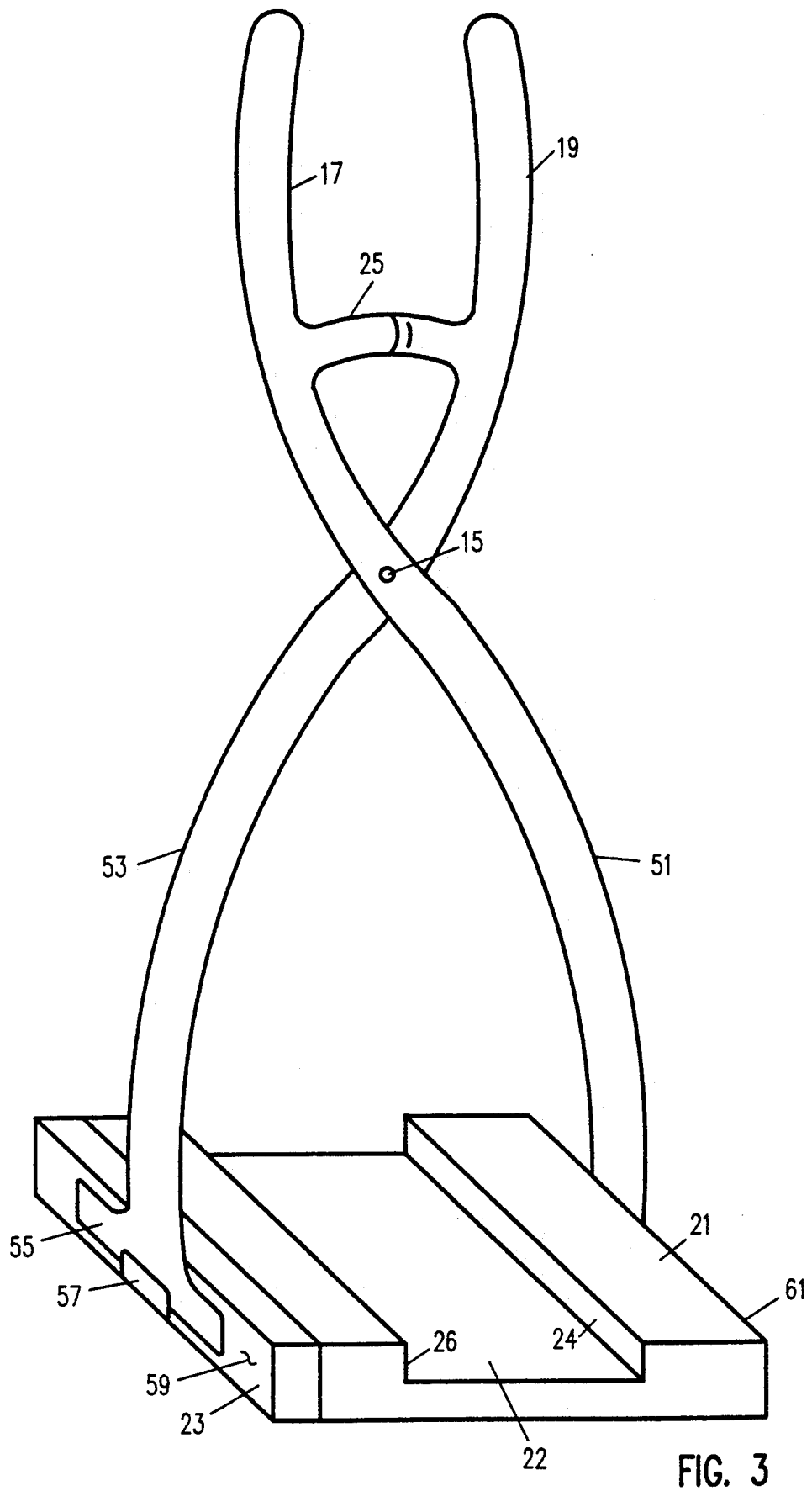
FIG. 3 is a perspective view of the tendon support clamp of FIG. 1 illustrating a second support configuration.

The lateral or outer plate 23 is generally a rectangularly shaped rod attached to one plier arm 13. The other plate 21 is referred to as the support plate 21 and is a generally flat rectangular shaped plate. The support plate 21 has a groove or channel 22 formed lengthwise in its upper surface (i.e., the surface facing the plier arm 11,13 intersection or pivot 15). The channel 22 may be of differing widths and depths to accommodate muscles of different dimensions. The channel walls 24, 26 may be slanted or vertical (as shown in FIG. 3). The lateral and support plates 23, 21, respectively, each have an inwardly facing face 33, 31, respectively, in opposing relationship with the other plate disposed in a spaced apart relationship forming a gap 35 therebetween when the clamp 10 is in an opened configuration. When the clamp 10 is in a closed configuration the opposing faces 31, 33 are in contact and clamped together.

The ratchet mechanism 25 is formed in a well-known manner, the ratchet arm 27 and the ratchet catch 29 each having a series of ratchet teeth 39 on their opposing faces in an engaging relationship. Engagement of the ratchet arm 27 and the ratchet catch 29 maintains the clamp 10 in a closed configuration with the plates 21, 23 clamped together. The ratchet arm 27 and ratchet catch 29 will engage each other so as to prevent the handle portions 17 and 19 from separating until such time as a user applies a twisting movement substantially parallel to the axis of the pivot bearing 15 to lift the ratchet arm 27 away from the ratchet catch 29 thus disengaging the ratchet teeth 39. The plier arms 11, 13 have sufficient overlap with respect to each other at the pivot bearing 15 to minimize twisting of the finger portions 21, 23 when the ratchet mechanism 25 is being engaged or disengaged. The tendon support clamp is constructed from a material having sufficient flexibility to prevent deformation to the plier arms 11, 13 during disengagement of the ratchet mechanism 25.

Referring now also to FIG. 3, a second embodiment of the tendon support clamp 10 having removeable plates 21, 23 is shown. The lateral plate 23 and the support plate 21 may be formed integrally with its respective plier arm 13, 11 (as shown in FIGS. 1 and 2) or may be removeable mounted to allow one set of plier arms 51, 53 to accommodate a set of several different sized plates 21, 23. Each plier arm 51, 53 comprises a handle portion 17, 19, respectively, at its proximal end and is joined to the other plier arm approximately at its midpoint by pivot bearing 15. The distal end of each plier arm 51, 53 includes an integrally formed mounting plate 55 which cooperates with a mounting bracket 57 in a well-known manner attached to the outwardly facing faces 59, 61 of the plates 23, 21. The lateral and support plates may be fabricated as a set, with several sets being available having support plates with differing widths and depths. Alternatively, a pair of plier arms 51, 53 may have the lateral plate 23 integrally formed with its respective plier arm and a set of matching removeable support plates 21 having different sized channels 22 available for interchangeable use with the other plier arm.

The plier arms of the tendon support clamp 10 are constructed from stainless steel or other suitable material to have sufficient flexibility to engage and disengage the ratchet mechanism 25 without permanent deformation of the plier arms or twisting of the plates 21, 23. Stainless steel also has sufficient resistance to corrosion to allow it to be used in surgical procedures. The lateral and support plates may be milled from standard size stainless steel stock or fabricated in some other suitable, well-known manner.

Figure 4:
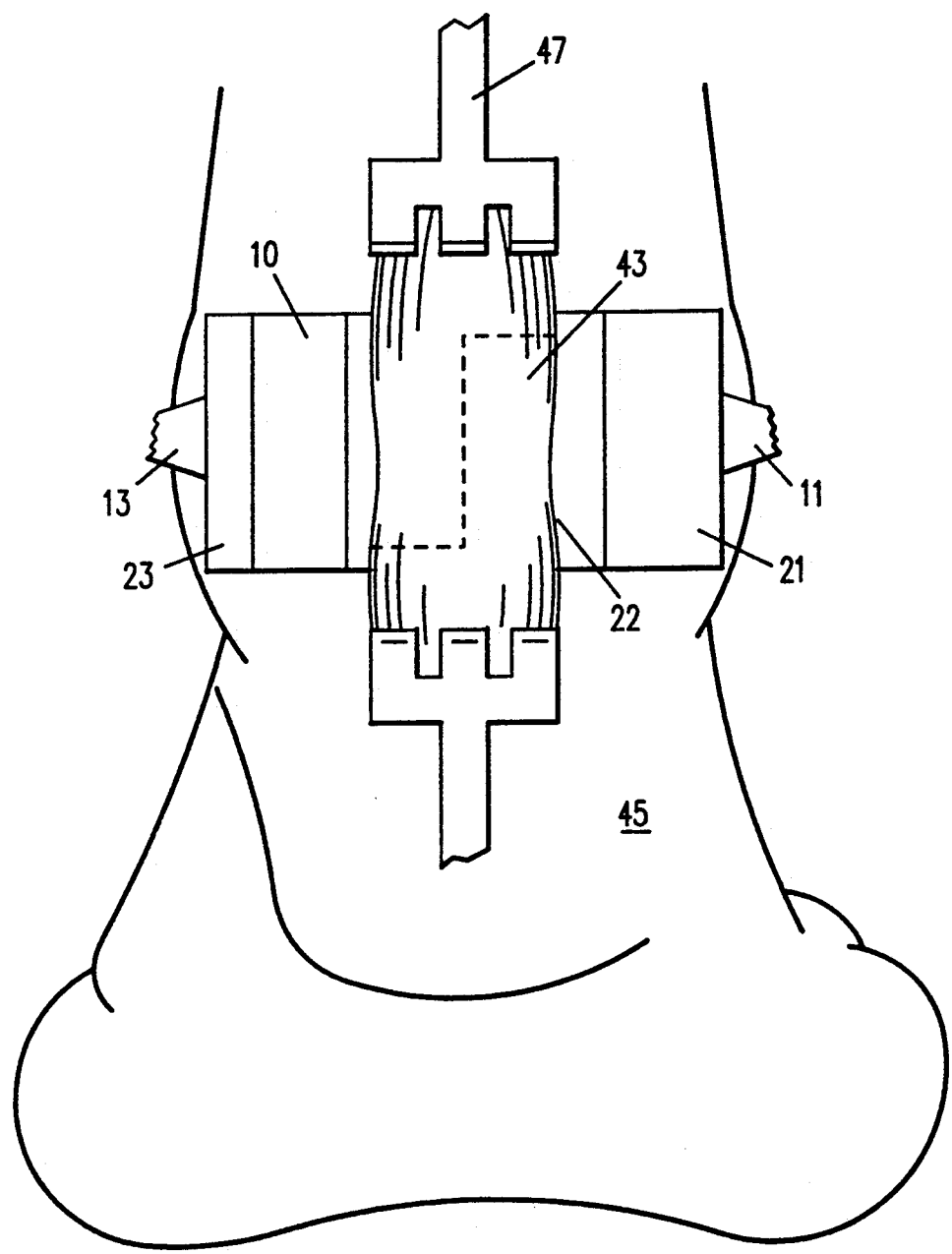
FIG. 4 is a perspective view of the tendon support clamp of FIG. 1 illustrating the tendon support clamp supporting an achilles tendon at the back of a human ankle.

Referring now also to FIG. 4, the tendon support clamp 10 is shown supporting an achilles tendon 43 in a human ankle 45 during a transectioning procedure to lengthen the tendon 43. With the tendon 43 exposed and accessible by spreader tool 47, the open clamp 10 (as shown in FIG. 2) is applied to the tendon. The tendon passes through the gap 35 formed between the opposing faces 31, 33. The clamp 10 is closed by engaging the ratchet mechanism 25 and the clamp 10 is positioned so that the tendon 43 lays in the channel 22 thus supporting the tendon 43 during the transectioning procedure. With the ratchet mechanism 25 engaged the clamp 10 is prevented from opening and the surgeon's hands are left free to perform the procedure. At the completion of the procedure, the ratchet mechanism 25 is disengaged and the clamp 10 removed.

Although the present invention has been described in its preferred form with a certain degree of particularity, it is understood that the present disclosure of the preferred embodiment has been by way of example and that numerous changes in the details of construction and the combination and arrangement of elements may be restored to without departing from the spirit and scope of the invention as hereinafter claimed.

I claim:

1. Apparatus for supporting in place a tendon or other smooth muscle during surgical procedures comprising:
    first and second elongated members;
    pivot means medially interconnecting said first and second elongated members;
    an elongated lateral block fixedly attached to a distal end of said first elongated member, said elongated lateral block extending transversely therefrom;
    an elongated support block fixedly attached to a distal end of said second elongated member, said elongated support block extending transversely therefrom being adjacent thereto and generally longitudinally parallel with said elongated lateral block, said elongated support block having an open channel formed in an upper surface thereof, said channel extending longitudinally substantially the length of said elongated support block, said channel being generally transverse to said first and second elongated members; and
    ratchet means disposed between said first and second elongated members coupling said elongated members together, said lateral block and said support block disposed in spaced apart relationship within said ratchet means are disengaged, said lateral block and said support block disposed adjacent to and in contact with the other along longitudinal facing edges thereof and urged toward each other when said ratchet means is engaged.

2. Apparatus as in claim 1 wherein said first and second elongated members each comprise a lower end and a handle portion at an upper end, said pivot means disposed between said handle portion and said lower end, said lateral block fixedly attached to said lower end of said first elongated member and said support block fixedly attached to said lower end of said second elongated member, said ratchet means disposed between said handle portions.

3. Apparatus as in claim 2 wherein said support block comprises a generally flat rectangular shaped plate oriented at substantially a with angle to said second elongated member, said lateral block and said support plate each having an inwardly facing face in opposing relationship with the other.

4. Apparatus as in claim 3 wherein said lateral block and said support plate are fabricated as an integral part of said first and second elongated members, respectively.

5. Apparatus as in claim 3 further comprising mounting means attached to said lower end of each of said first and second elongated members for removeably attaching said lateral block and said support plate to its respective elongated member.

6. Apparatus as in claim 5 wherein said mounting means comprise a mounting plate integrally formed at said lower end of said first and second elongated members and attachment means fixedly attached to an outside face of said lateral block and said support plate, said mounting plate adapted to cooperate with said attachment means for removeably attaching said lateral block san said support plate to said first and second elongated members, respectively.

7. Apparatus as in claim 1 wherein said apparatus is fabricated from stainless steel.

* * * * *